(12) United States Patent
Gelbart

(10) Patent No.: US 6,340,817 B1
(45) Date of Patent: Jan. 22, 2002

(54) INSPECTION METHOD FOR UNPOPULATED PRINTED CIRCUIT BOARDS

(75) Inventor: Daniel Gelbart, Vancouver (CA)

(73) Assignee: Creo S.R.L., Holetown (BB)

( * ) Notice: Subject to any disclaimer, the term of this patent is extended or adjusted under 35 U.S.C. 154(b) by 0 days.

(21) Appl. No.: 09/301,375

(22) Filed: Apr. 23, 1999

(51) Int. Cl.[7] ............................................... G01N 21/71
(52) U.S. Cl. .................................. 250/341.6; 250/341.8
(58) Field of Search ........................... 250/341.6, 341.1, 250/341.8, 339.11, 330

(56) References Cited

U.S. PATENT DOCUMENTS

| | | | | |
|---|---|---|---|---|
| 3,463,007 A | * | 8/1969 | Jones et al. .................... 73/355 |
| 3,803,413 A | * | 4/1974 | Vanzetti et al. ............. 250/338 |
| 3,868,508 A | * | 2/1975 | Lloyd .......................... 250/330 |
| 4,481,418 A | * | 11/1984 | Vanzetti et al. ............. 250/338 |
| 4,507,605 A | * | 3/1985 | Geisel ........................... 324/73 |
| 4,578,810 A | * | 3/1986 | MacFarlane ................... 382/8 |
| 4,668,982 A | * | 5/1987 | Tinnerino .................... 358/101 |
| 4,792,683 A | * | 12/1988 | Chang et al. ............... 250/341 |
| 4,965,451 A | * | 10/1990 | Sölter .......................... 250/330 |
| 5,208,528 A | * | 5/1993 | Quintard .................. 324/158 R |
| 5,495,535 A | * | 2/1996 | Smilansky et al. .......... 382/145 |
| 6,072,518 A | * | 6/2000 | Gelbart ....................... 347/239 |

FOREIGN PATENT DOCUMENTS

JP 07325120 * 12/1995 ............ G01R/3/02

* cited by examiner

Primary Examiner—Georgia Epps
Assistant Examiner—Richard Hanig
(74) Attorney, Agent, or Firm—Oyen Wiggs Green & Mutala

(57) ABSTRACT

A method and apparatus for inspection of unpopulated printed circuit boards is disclosed. A printed circuit board is mounted on a mobile base capable of scanning on at least one direction. During a scan, the printed circuit board moves with respect to a heater and a portion of the board's surface, including both tracks and substrate, is heated. After heating, but within seconds of removing the heat source, the board surface is analyzed by an infrared (IR) sensitive camera. The different intensities of IR emissions allow for discrimination between the traces and the substrate and provide a means of detecting defects on the board. Defects are detected either by comparison to a database used for production of the boards or by design rule checking.

29 Claims, 2 Drawing Sheets

INSPECTION METHOD FOR UNPOPULATED PRINTED CIRCUIT BOARDS

FIELD OF THE INVENTION

This invention relates to an inspection method and apparatus for detecting defects on unpopulated printed circuit boards.

BACKGROUND OF THE INVENTION

Printed circuit boards are made out of many different materials. Typically, the substrate of a board is made out of epoxy-fiberglass, Kapton (polyimide), Teflon, or polystyrene, but other materials are also used. Typically, the tracks (or the current carrying areas of the board) are made of copper, but can be made of other conducting materials. Traditional optical methods of viewing the unpopulated boards do not function well, particularly when the copper traces are oxidized, because of poor optical contrast between the traces and the substrate.

A typical unpopulated printed circuit board is depicted schematically in FIG. 1. The substrate 10A of board 10 has traces 11 which form circuit patterns thereon. Occasionally, due to processing abnormalities or other events, the traces 11 on the board 10 will have open circuits 13 where a trace is broken, or short circuits 12 where two traces have joined. As such, there is a need for a method of viewing and inspecting of unpopulated printed circuit boards that can overcome the lack of optical contrast between the traces and the substrate and can locate open 13 or short circuits 12. Other defects are pinholes, notches, size variations, areas of partial etching and many others.

For purposes of the ensuing discussion and claims, the word "unpopulated" should be understood to refer to printed circuit boards which are substantially bare and have not been assembled with many components.

Several U.S. patents describe techniques use heat emissions to help inspect "populated" circuit boards (i.e. those that contain components). U.S. Pat. No. 5,208,528 discloses a method of inspecting the solder joints on a populated board by heating the board and then recording its thermographic image. U.S. Pat. No. 4,792,683 concerns a method of checking the electronic integrity of solder joints on a populated circuit board by pulse heating the board with radiant energy and then measuring the temperature oscillation of the solder joints by measuring their infrared emissions. U.S. Pat. No. 3,463,007 discloses a method of detecting the thermal radiation pattern of a populated, but faulty, circuit board and comparing it to a reference board to find malfunctioning component(s) on the board. U.S. Pat. No. 3,868,508 describes an inspection method similar to that of the '007 invention with a digital approach. U.S. Pat. No. 3,803,413 describes a similar procedure to the '007 and the '508 patents except that the reference emission pattern is preprogrammed. The '007, '508 and '413 patents do not teach that heat can be applied to the board. U.S. Pat. No. 4,481,418 discloses the use of a fiber optic system to sequentially apply heat and to measure the radiation profile from individual solder joints on a printed circuit board. All of the aforementioned patents involve the testing and inspection of populated circuit boards.

U.S. Pat. No. 4,668,982 discusses an improvement to the above systems by employing an optical method to compensate for distortion between a test printed circuit board and a reference. The optical method involves comparing fiducial marks on the corners of the test board and the reference.

U.S. Pat. No. 5,495,535 discloses an optical method for imaging a unpopulated printed circuit board and comparing it to a reference to improve the board's registration. U.S. Pat. No. 4,578,810 describes an optical method for inspecting unpopulated printed circuit boards using an array of CCD optical sensors. A drawback with the '810 process is poor optical contrast between the traces and the substrate, as mentioned above.

Japanese Patent Number JP07325120 discloses a method for detecting the integrity of contact holes on a printed circuit board. These holes are typically coated with a conductive surface that extends through the board. A contact hole is heated on one side of the board by irradiation with light and the differential heat emission profile is measured between the alternate sides of the board to search for defective contact holes having open circuits. Although the method discloses heating printed circuit boards and sensing the emissions for open circuits, the method is limited to contact holes and is based on the differential heat emission profile on the different sides of the board.

U.S. Pat. No. 4,965,451 discloses a technique where an electromagnetic exciting beam is divided and used to heat isolated cells on a solid "workpiece". The resulting temperature profile (measured as the intensity of infrared radiation) is used to provide information about the surface and inner structure of the workpiece. The exciting beam is subdivided using a mask, which separates the beam into component beams, each component beam illuminating a single cell. The infrared heat radiation is measured during the heating and cooling of the workpiece and is compared to reference profiles for unflawed workpieces. The process does not use the measured infrared emission data directly to discriminate between two different materials in the workpiece, but rather it compares the data to a reference. As such, it is not well suited for measuring a workpiece with varied surface structure such as a printed circuit board with traces and substrate. The '451 process does not disclose a method of searching for breaks or short circuits on a printed circuit board, but simply for abnormalities on the surface and inner structure of a solid workpiece.

None of the above mentioned patents disclose a method or apparatus for inspecting the surface of an unpopulated printed circuit board by heating its surface in a first step and then subsequently measuring the resulting infrared emission profile to search for short or open circuits based on the different intensities of the emissions from the traces and the substrate.

Accordingly, there is a need for a process and apparatus that permits rapid inspection of unpopulated printed circuit boards for open and short circuits.

SUMMARY OF THE INVENTION

This invention provides a process and apparatus for the rapid inspection of unpopulated printed circuit boards for faults such as open and short circuits. In preferred embodiments of the invention, the method and apparatus apply heat to a circuit board surface and subsequently identify traces by differential infrared emissions between the traces and the substrate. Accordingly, one aspect of the invention provides a method of inspecting and detecting defects on an unpopulated printed circuit board having metallic conductors on an electrically insulating substrate. The method comprises several steps. The first step involves changing the surface temperature of a portion of the printed circuit board. After the temperature is changed, then the surface of the printed circuit board is scanned with a sensor. The infrared sensor is sensitive to wavelengths above 1 micron and detects an emission profile from the portion of the printed circuit board with the changed temperature. Finally, the method involves discriminating between the metallic conductors and the substrate on the portion of the printed circuit board based on differences in their emission profiles.

Advantageously, the temperature changing may be accomplished by heating or cooling. An extra step may be added wherein a short time delay is introduced between the changing of the temperature the scanning of the printed circuit board with the sensor. Preferably, the infrared sensor is a microbolometer array. The temperature changing step may be effected either by bringing a hot object into proximity with the printed circuit board or by directing a stream of hot air at the board. Such a heat source may also be scanned by having relative motion between the board and the heat source. The data extracted from the discriminating step may be used to locate defects either by comparison to data used for generating the board or by searching for design rule violations.

The invention also discloses an apparatus for inspecting and detecting defects on an unpopulated printed circuit board having metallic conductors on an electrically insulating substrate. The apparatus comprises a flat bed operative to receive the board and capable of scanning on a primary scan axis. A heat source, also included, is operative to heat a portion of the board as it is scanned past the heat source. A sensor is located adjacent to the heat source and is operative to detect an emission profile of wavelengths greater than 1 micron from the board after it is heated. Finally, the apparatus includes a discrimination system which is operative to interpret data from the sensor and discriminate between the metallic conductors and the substrate on the board.

The invention also concerns an alternate apparatus, which comprises a cylindrical drum operative to receive the printed circuit board on an outer cylindrical surface thereof and capable of rotating about a central axis. A heat source is located adjacent to the drum and is operative to heat a portion of the board as it is scanned past the heat source during a rotation about the central axis. Once again, a sensor is located adjacent to the heat source and is operative to detect an emission profile of wavelengths greater than 1 micron from the printed circuit board after it is heated. A discrimination system is also included and is operative to interpret data from the sensor and discriminate between the metallic conductors and the substrate.

Advantageously, these methods and apparatus may be used for detecting short circuits or open circuits.

DESCRIPTION OF THE PREFERRED EMBODIMENT

Figure 1:
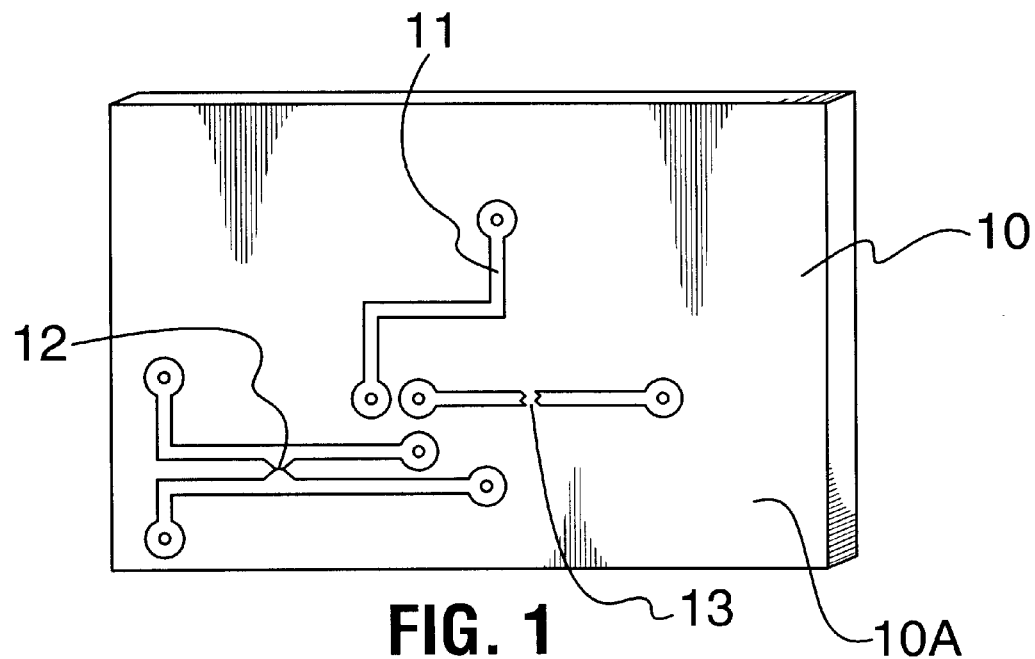
FIG. 1 depicts a typical printed circuit board and the open and short circuit problems that may occur thereon.
Figure 2:
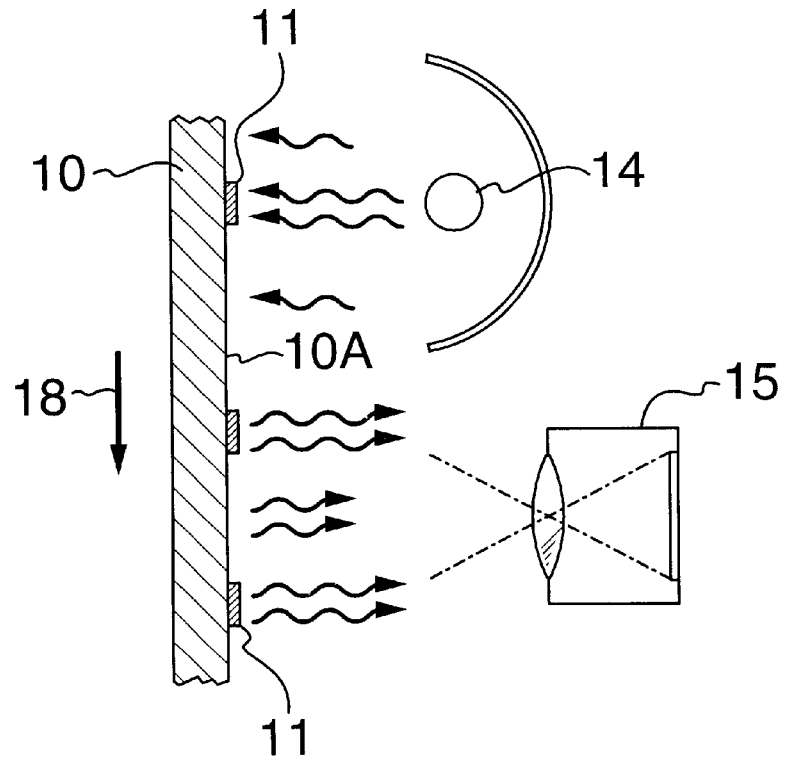
FIG. 2 shows the effect of heating the printed circuit board and the differential heat emission from the traces and the substrate of the printed circuit board.

The invention herein disclosed involves the heating of a printed circuit board. This heating process is depicted in FIG. 2. A heating lamp 14 heats the surface of the printed circuit board 10 and the heat is absorbed by both the copper traces 11 and the substrate 10A. Shortly after the heat source is removed, the heat radiates quickly from the copper traces 11, but remains trapped inside the non-metallic substrate 10A for a longer period of time. The metallic areas cool down faster and can be clearly distinguished from the non-metallic areas, regardless of the color and texture of either area. Clearly cooling can be used instead of heating to alter the surface temperature. In this case, the metallic areas will appear warmer than the substrate.

Although the above explanation is believed to be the reason for the differential infrared emission profiles from the traces 11 and the substrate 10A, the invention does not depend on that reasoning and should be understood to have novelty which is independent of the above explanation.

Figure 3:
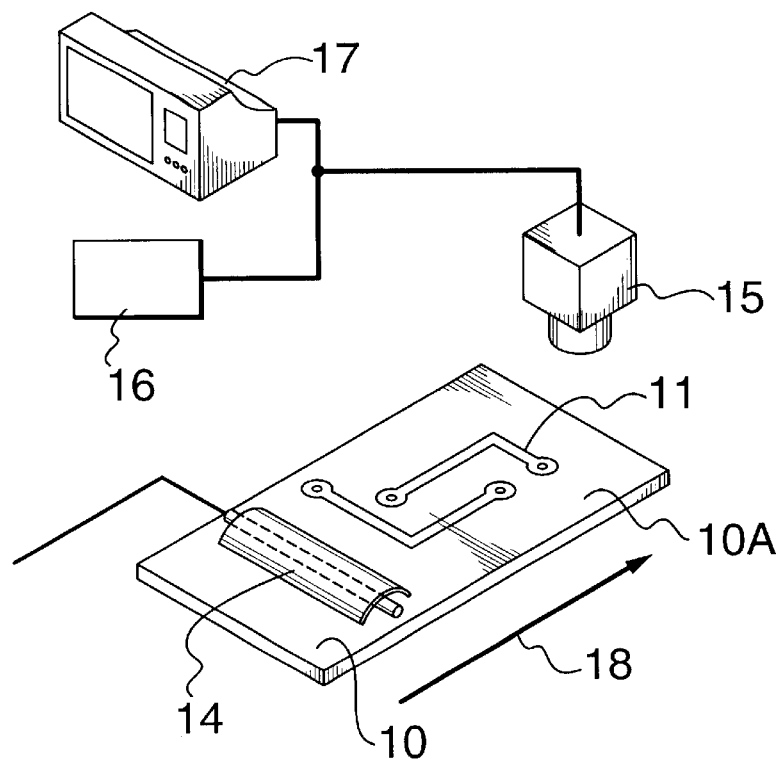
FIG. 3 depicts an embodiment of the present invention on a flat scanning surface.

An embodiment of the invention is depicted in FIGS. 2 and 3. The printed circuit board 10 is mounted on a flat surface and is scanned in a direction 18 with respect to a heating element 14 and an infrared sensitive camera 15. The camera 15 is positioned adjacent to the heating element 14, such that the circuit board 10 being scanned passes under the heater 14 prior to passing under the camera 15. The traces 11 and the substrate 10A are heated as they pass under the heater 14 and shortly thereafter, as they pass under the infrared sensitive camera 15, they are cooling down. The camera 15 senses the heat emission profile of the substrate 10 and the traces 11 and relays the information to a display unit 17 and/or defect detection electronics 16.

Figure 4:
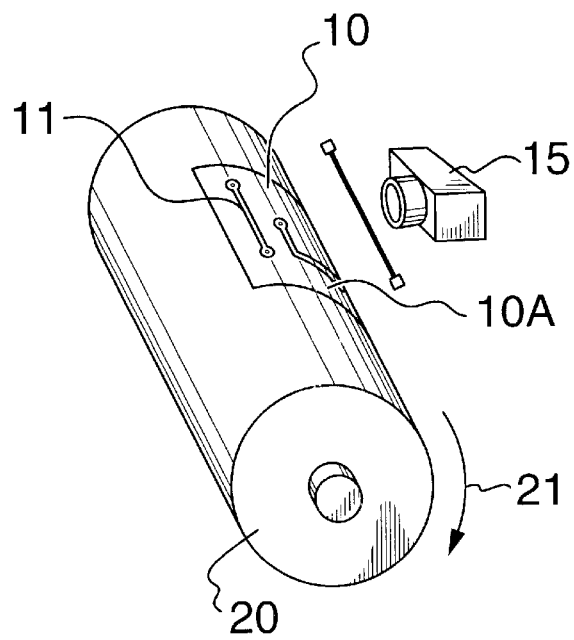
FIG. 4 depicts an embodiment of the present invention on a cylindrical or drum scanning surface.

FIG. 4 depicts an embodiment of the invention where the printed circuit board 10 is mounted on a rotating cylindrical drum 20. The rotation of the drum 20 effectively scans the board 10 past the heat source 14 and the infrared camera 15.

Two methods of defect detection, well known in the art, are used to search for short and open circuits. The first method involves comparison to a database used for making the particular board. In such a method, areas detected (by their emission profile) as traces are compared to trace areas in the database. If there are notable differences, particularly short or open circuits, then the board is rejected. A second detection method involves design rule checking. Design rules for printed circuit boards include characteristics such as, conductor width, conductor spacing, hole sizes and others. In a design rule detection scheme, the electronic profile of the entire board would be scanned and any breach of a design rule would cause the board to be rejected. The advantage over the database method is that precise registration is not required.

The invention was employed in a number of experimental tests. Two examples are described below.

EXAMPLE 1

A printed circuit board having an epoxy-fiberglass substrate and copper traces was covered with a thin layer of opaque black paint. The surface was heated with a hot wire heater to about 80° C. and then viewed with an AGEMA Model 570 Microbolometer camera with a resolution of 320×240 pixels. The infrared camera was used to view the surface within 1–3 seconds after the heat source was removed. The copper was clearly differentiable from the substrate. Since the board was covered with paint, this example indicates a high immunity to surface contamination.

EXAMPLE 2

The same equipment was used to inspect printed circuit boards having substrates of Teflon and Kapton (Polyimide).

Once again, the copper conductors appeared as clear lines that were discernible at the same threshold as copper on the epoxy-fiberglass substrate. Consequently, the example indicates that the method is not sensitive to the type of material used as a substrate.

What is claimed is:

1. A method of inspecting and detecting defects on an unpopulated printed circuit board having metallic conductors on an electrically insulating substrate, which method comprises the steps of:
   (a) changing a surface temperature of a portion of said printed circuit board;
   (b) scanning the surface of said printed circuit board with a sensor, said sensor being sensitive to wavelengths above 1 micron and detecting an emission profile from said portion of the printed circuit board; and
   (c) discriminating between the metallic conductors and the substrate on said portion of the printed circuit board based on differences in said emission profile.

2. A method according to claim 1, wherein said changing step is accomplished using heating as a means of temperature change.

3. A method according to claim 1, wherein said changing step is accomplished using cooling as a means of temperature change.

4. A method according to claim 1, wherein an extra step of introducing a short time delay between said changing and said scanning steps.

5. A method according to claim 1, wherein said sensor is a microbolometer array.

6. A method according to claim 1, wherein said changing step is effected by bringing a hot object into proximity with said portion of the printed circuit board, while having relative motion between said printed circuit board and said hot object.

7. A method according to claim 1, wherein said changing step is effected by directing a stream of hot air at said portion of the printed circuit board, while having relative motion between said printed circuit board and said stream of hot air.

8. A method according to claim 1, wherein data extracted from said discriminating step is used to locate defects.

9. A method according to claim 8, wherein said defects are located by comparison to data used for generating said printed circuit board.

10. A method according to claim 8, wherein said defects are located by searching for design rule violations.

11. An apparatus for inspecting and detecting defects on an unpopulated printed circuit board having metallic conductors on an electrically insulating substrate, which apparatus comprises:
    (a) a flat bed operative to receive said printed circuit board and capable of scanning on a primary scan axis and a secondary axis;
    (b) a heat source operative to heat a portion of said printed circuit board as it is scanned past said heat source during a scan along the primary scan axis;
    (c) a sensor located adjacent to said heat source, said sensor operative to detect an emission profile of wavelengths greater than 1 micron from said portion of the printed circuit board after it is scanned past said heat source; and
    (d) a discrimination system which is operative to interpret data from said sensor and discriminate between said metallic conductors and said substrate on said portion of the printed circuit board.

12. An apparatus according to claim 11, wherein said heat source is a hot object which is brought into proximity with said portion of the printed circuit board.

13. An apparatus according to claim 11, wherein said heat source is a stream of hot air which is directed at said portion of the printed circuit board.

14. An apparatus according to claim 11, which further comprises an electronic defect detection system which is operative to take data from said discrimination system and locate defects.

15. An apparatus according to claim 14, wherein said defects comprise at least one of: short circuits and open circuits.

16. An apparatus according to claim 14, wherein said electronic defect detection system is operative to locate defects by comparison to data used to generate said printed circuit board.

17. An apparatus according to claim 14, wherein said electronic defect detection system is operative to locate defects by detecting design rule violations.

18. An apparatus for inspecting and detecting defects on an unpopulated printed circuit board having metallic conductors on an electrically insulating substrate, which apparatus comprises:
    (a) a cylindrical drum operative to receive said printed circuit board on an outer cylindrical surface thereof and capable of rotating about a central axis;
    (b) a heat source operative to heat a portion of said printed circuit board as it is scanned past said heat source during a rotation about said central axis;
    (c) a sensor located adjacent to said heat source, said sensor operative to detect an emission profile of wavelengths greater than 1 micron from said portion of the printed circuit board after it is scanned past said heat source; and
    (d) a discrimination system which is operative to interpret data from said sensor and discriminate between said metallic conductors and said substrate on said portion of the printed circuit board.

19. An apparatus according to claim 18, wherein said heat source is a hot object which is brought into proximity with said portion of the printed circuit board.

20. An apparatus according to claim 18, wherein said heat source is a stream of hot air which is directed at said portion of the printed circuit board.

21. An apparatus according to claim 18, which further comprises an electronic defect detection system which is operative to take data from said discrimination system and locate defects.

22. An apparatus according to claim 21, wherein said defects comprise at least one of short circuits and open circuits.

23. An apparatus according to claim 21, wherein said electronic defect detection system is operative to locate defects by comparison to data used to generate said printed circuit board.

24. An apparatus according to claim 21, wherein said electronic defect detection system is operative to locate defects by detecting design rule violations.

25. A method for inspecting and detecting defects on an unpopulated printed circuit board having metallic conductors on an electrically insulating substrate, the method comprising:
    (a) changing a surface temperature of a portion of a printed circuit board;
    (b) scanning the surface of the printed circuit board with a sensor which is sensitive to wavelengths above 1 micron and, at the sensor, detecting electromagnetic emissions having wavelengths in excess of 1 micron from points in the portion of the printed circuit board; and, (c) determining a two-dimensional extent of the metallic conductors in the portion of the circuit board by associating at least some of the points with the metallic conductors based on differences in the electromagnetic emissions between the points.

26. An apparatus for inspecting and detecting defects on an unpopulated printed circuit board having metallic conductors on an electrically insulating substrate, the apparatus comprising:

(a) a heat source operative to heat a portion of a printed circuit board;

(b) a sensor sensitive to wavelengths above 1 micron located to sense electromagnetic emissions from points in the portion of the printed circuit board and to generate an output signal in response thereto;

(c) a discrimination system connected to receive the output signal and determine a two-dimensional extent of the metallic conductors in the portion of the circuit board by associating at least some of the points with the metallic conductors based on differences in the electromagnetic emissions between the points.

27. A method for inspecting and detecting defects on an unpopulated printed circuit board having metallic conductors on an electrically insulating substrate, the method comprising:

(a) changing a surface temperature of a portion of a printed circuit board;

(b) scanning the surface of the printed circuit board with a sensor which is sensitive to wavelengths above 1 micron and, at the sensor, detecting electromagnetic emissions having wavelengths in excess of 1 micron from a plurality of points in the portion of the printed circuit board, the plurality of points including first points corresponding to metallic conductors and second points corresponding to exposed substrate;

(c) discriminating between the first and second points on the basis of the emissions detected at the sensor;

(d) generating from the first and second points data representing a two-dimensional extent of the metallic conductors in the portion of the circuit board; and, (e) checking the data for indications of defects in the circuit board.

28. The method of claim 27 wherein checking the data comprises checking the two-dimensional extent of the metallic conductors for violations of a set of design rules.

29. The method of claim 27 wherein checking the data comprises comparing the two-dimensional extent of the metallic conductors with data used for generating the circuit board.

* * * * *